(12) United States Patent
Wu

(10) Patent No.: US 9,649,218 B2
(45) Date of Patent: *May 16, 2017

(54) SPERM COLLECTOR WITH SQUEEZING FUNCTION

(71) Applicant: Wei Wu, Huzhou (CN)

(72) Inventor: Wei Wu, Huzhou (CN)

(73) Assignee: LOVER HEALTH SCIENCE AND TECHNOLOGY CO., LTD., Huzhou (CN)

( * ) Notice: Subject to any disclaimer, the term of this patent is extended or adjusted under 35 U.S.C. 154(b) by 879 days.

This patent is subject to a terminal disclaimer.

(21) Appl. No.: 13/892,281

(22) Filed: May 12, 2013

(65) Prior Publication Data

US 2013/0253458 A1    Sep. 26, 2013

Related U.S. Application Data

(63) Continuation of application No. 13/165,828, filed on Jun. 22, 2011, now Pat. No. 8,475,422.

(30) Foreign Application Priority Data

Feb. 22, 2011    (CN) ............... 2011 2 0043933 U

(51) Int. Cl.
| A61F 5/41 | (2006.01) |
| A61F 5/453 | (2006.01) |
| A61B 10/00 | (2006.01) |
| A61H 19/00 | (2006.01) |

(52) U.S. Cl.
CPC .......... *A61F 5/453* (2013.01); *A61B 10/0058* (2013.01); *A61F 5/41* (2013.01); *A61H 19/32* (2013.01); *A61H 2201/0228* (2013.01); *A61H 2201/105* (2013.01); *A61H 2201/5082* (2013.01)

(58) Field of Classification Search
CPC .................................................. A61H 19/32
USPC ............. 604/317, 349, 350–353; 600/38–39; 128/844, 917–918
See application file for complete search history.

(56) References Cited

U.S. PATENT DOCUMENTS

| 2,686,519 A | * | 8/1954 | Westerman | .......... A61D 19/021 604/347 |
| 3,602,923 A | * | 9/1971 | Girala | .......... A61F 5/4404 4/144.1 |
| 4,074,712 A | * | 2/1978 | Wright | .......... A61F 6/04 600/39 |
| 4,312,350 A | * | 1/1982 | Doan | .......... A61B 10/0058 604/349 |
| 4,407,275 A | * | 10/1983 | Schroeder | .......... A61F 5/41 600/38 |

(Continued)

*Primary Examiner* — Paula L. Craig
(74) *Attorney, Agent, or Firm* — Anova Law Group, PLLC

(57) ABSTRACT

A sperm collector is provided. The sperm collector includes an insert having a penis insertion passage. The sperm collector also includes a container having an outer shell forming an inside chamber. The outer shell has at least one opening. The inside chamber is configured to accommodate the insert. The sperm collector also includes a top end cover capable of being engaged with the container. The sperm collector further includes an elastic pressing unit disposed on the outer shell and coupled to the insert through the opening on the outer shell. The elastic pressing unit is configured to transmit pressure to the insert through the opening on the outer shell.

13 Claims, 4 Drawing Sheets

(56) References Cited

U.S. PATENT DOCUMENTS

| | | | | |
|---|---|---|---|---|
| 4,429,689 A * | 2/1984 | Yanong | A61F 5/41 | 600/39 |
| 4,580,553 A * | 4/1986 | Laib | A61H 19/00 | 198/819 |
| 4,620,531 A * | 11/1986 | Dyer | A61D 19/021 | 604/349 |
| 4,744,352 A * | 5/1988 | Emery | A61D 19/021 | 604/349 |
| 4,846,197 A * | 7/1989 | Benjamin | A61F 6/04 | 128/844 |
| D330,762 S * | 11/1992 | Anderson | D24/108 | |
| 5,377,692 A * | 1/1995 | Pfeil | A61F 6/04 | 128/844 |
| 5,437,652 A * | 8/1995 | Anatolievich | A61D 19/021 | 604/349 |
| 5,454,379 A * | 10/1995 | Shepherd | A61F 6/02 | 128/842 |
| 5,458,559 A * | 10/1995 | Gauntlett | A61H 19/00 | 128/830 |
| 5,501,650 A * | 3/1996 | Gellert | A61F 5/41 | 600/38 |
| 5,524,638 A * | 6/1996 | Lyons | A61F 5/41 | 128/844 |
| 5,540,670 A * | 7/1996 | Lindholm-Ventola | A61D 19/021 | 600/575 |
| 5,669,869 A * | 9/1997 | Strom | A61F 5/41 | 600/38 |
| 5,685,871 A * | 11/1997 | Lindholm-Ventola | A61D 19/021 | 604/349 |
| 5,695,446 A * | 12/1997 | Lindholm-Ventola | A61D 19/021 | 600/38 |
| 5,782,818 A * | 7/1998 | Shubin | A61B 10/0058 | 600/38 |
| 5,885,205 A * | 3/1999 | Kassman | A61F 5/41 | 128/842 |
| 5,885,233 A * | 3/1999 | Adachi | A61H 19/32 | 600/38 |
| 6,090,088 A * | 7/2000 | Nichols | A61D 19/021 | 119/838 |
| 6,113,532 A * | 9/2000 | Yap | A61F 5/41 | 600/38 |
| 6,149,580 A * | 11/2000 | Dabney | A61H 19/32 | 600/38 |
| 6,419,665 B1 * | 7/2002 | Cohen | A61F 5/453 | 604/349 |
| 6,436,031 B1 * | 8/2002 | Salib | A61F 5/41 | 600/39 |
| 6,531,771 B1 * | 3/2003 | Schoenstein | H01L 23/36 | 257/720 |
| 6,599,236 B1 * | 7/2003 | Castro | A61H 19/44 | 600/38 |
| 7,217,239 B1 * | 5/2007 | Dyer | A61D 19/021 | 600/33 |
| 8,475,422 B2 * | 7/2013 | Wu | A61B 10/0058 | 600/38 |
| 2002/0032419 A1 * | 3/2002 | Barth | A61D 19/021 | 604/349 |
| 2003/0083598 A1 * | 5/2003 | Kobayashi | A61F 5/41 | 601/70 |
| 2004/0039248 A1 * | 2/2004 | Vayer | A61D 19/021 | 600/38 |
| 2005/0283044 A1 * | 12/2005 | Chang | A61F 5/41 | 600/38 |
| 2006/0229494 A1 * | 10/2006 | Wu | A61F 5/41 | 600/38 |
| 2006/0235266 A1 * | 10/2006 | Nan | A61F 5/41 | 600/38 |
| 2006/0264856 A1 * | 11/2006 | Wong | A61H 19/00 | 604/349 |
| 2007/0261700 A1 * | 11/2007 | Chan | A61F 6/04 | 128/844 |
| 2008/0004577 A1 * | 1/2008 | Matsuura | A61B 10/0058 | 604/317 |
| 2008/0065033 A1 * | 3/2008 | Matsuura | A61B 10/0045 | 604/349 |
| 2008/0082028 A1 * | 4/2008 | Blevins | A61H 19/34 | 601/72 |
| 2008/0230073 A1 * | 9/2008 | Nan | A61H 19/50 | 128/844 |
| 2008/0294130 A1 * | 11/2008 | Simmet | A61D 19/021 | 604/349 |
| 2009/0069629 A1 * | 3/2009 | Uson Calvo | A61F 5/41 | 600/38 |
| 2009/0137974 A1 * | 5/2009 | Yvoz | A61D 19/021 | 604/349 |
| 2009/0318755 A1 * | 12/2009 | Adams | A61F 5/41 | 600/41 |
| 2010/0126513 A1 * | 5/2010 | Hui | A61F 6/04 | 128/844 |
| 2011/0009691 A1 * | 1/2011 | Stevens | A61H 19/44 | 600/38 |

\* cited by examiner

SPERM COLLECTOR WITH SQUEEZING FUNCTION

CROSS-REFERENCES TO RELATED APPLICATIONS

This application is a continuation of U.S. patent application Ser. No. 13/165,828 filed on Jun. 22, 2011, the entire contents of which are hereby incorporated by reference.

BACKGROUND

The present invention relates to a sperm collector and a method for using the same and, more specifically, relates to a sperm collector with squeezing function and a method for using the same.

Currently existing sperm collector mainly comprises a soft rubber body provided with a penis insertion passage and a container body provided with at least an end cover to receive the soft rubber body. When the end cover is closed, the soft rubber body is confined within a cavity formed by the end cover and the container body. When the end cover is opened, a front end portion of the soft rubber body protrudes out of the container body's opening so that a user of the sperm collector could grab the container body and uses the sperm collector directly. Sperm collector in such a structure may have certain disadvantages. Firstly, as the container body has a certain degree of hardness (to support the soft rubber body), the user is not able to press against an outer wall of the container body to squeeze the penis insertion passage of the soft rubber body received therein and therefore the stimulation effect on penis is not sufficient. Secondly, due to the lack of heating function, it may cause discomfort to the penis when the sperm collector is used in an environment under relatively low temperature (for example winter) and sperm collection effect is therefore affected. Thirdly, without an enhancing component, the user is not easy to reach a climax when using the sperm collector.

The disclosed sperm collector and the method for using the same are directed at solving one or more problems set forth above and other problems.

BRIEF MARY OF THE INVENTION

One aspect of the present disclosure provides a sperm collector. The sperm collector includes an insert having a penis insertion passage. The sperm collector also includes a container having an outer shell forming an inside chamber. The outer shell has at least one opening. The inside chamber is configured to accommodate the insert. The sperm collector also includes a top end cover capable of being engaged with the container. The sperm collector further includes an elastic pressing unit disposed on the outer shell and coupled to the insert through the opening on the outer shell. The elastic pressing unit is configured to transmit pressure to the insert through the opening on the outer shell.

Another aspect of the present disclosure provides a method of using a sperm collector. The sperm collector includes an insert having a penis insertion passage, a container having an outer shell forming an inside chamber, the outer shell having at least one opening, wherein the inside chamber is configured to accommodate the insert, a top end cover capable of being engaged with the container, and an elastic pressing unit disposed on the outer shell and coupled to the insert through the opening on the outer shell, wherein the elastic pressing unit is configured to transmit pressure to the insert through the opening on the outer shell. The method includes removing the top end cover and pressing on the elastic pressing unit to apply pressure on the insert.

Other aspects of the present disclosure can be understood by those skilled in the art in light of the description, the claims, and the drawings of the present disclosure.

DETAILED DESCRIPTION OF THE INVENTION

Figure 1:
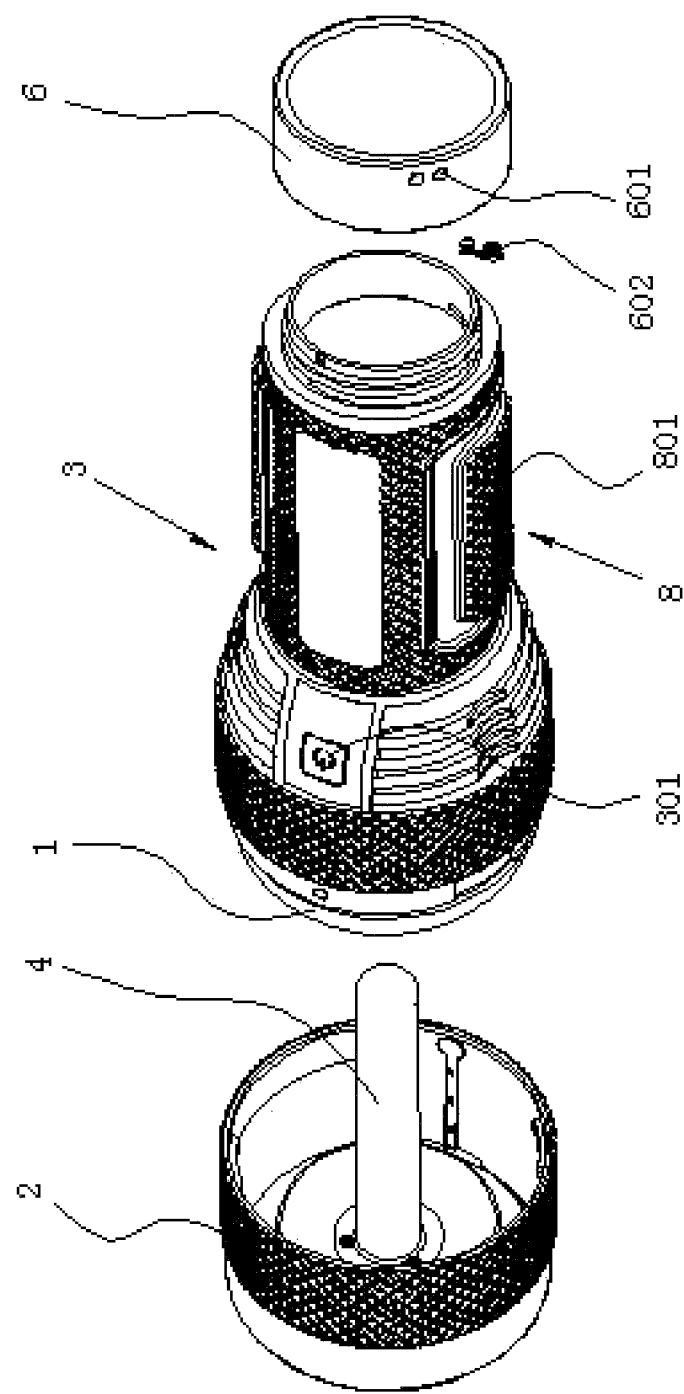
FIG. 1 is a three dimensional illustration of a structure of an exemplary sperm collector consistent with the disclosed embodiments in an exploded view.
Figure 2:
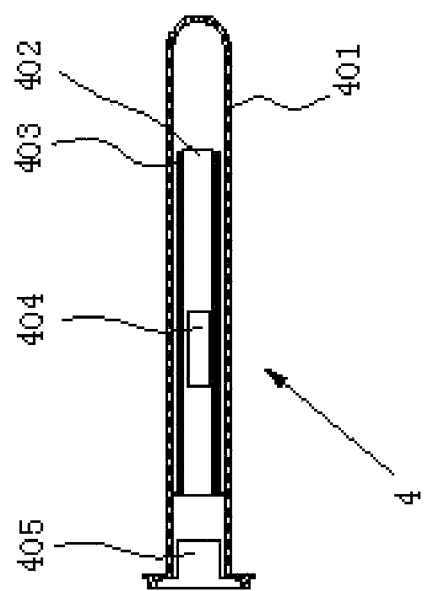
FIG. 2 is an illustration of a structure of an exemplary heating rod consistent with the disclosed embodiments as shown in FIG. 1.

One objective of the present invention is to provide a sperm collector. The sperm collector may have a squeezing function. By pressing against the sperm collector, the penis insertion passage of the sperm collector could be pressed so as to increase stimulation to penis and achieve better effect of sperm collection.

An exemplary sperm collector consistent with the disclosed embodiments may include an insert with a penis insertion passage and a container with at least a top end cover. The container has an outer shell that forms an inside chamber, which is configured to accommodate the insert. When the top end cover and the container are engaged, the insert is confined within the inside chamber. When the top end cover is disengaged, a front end portion of the insert may protrude out of an opening of the container.

The exemplary sperm collector consistent with the disclosed embodiments may include an elastic pressing unit. In certain embodiments, the elastic pressing unit may include a handle sleeve. The handle sleeve may surround the outer shell of the container. The container may have at least one opening on the outer shell. The elastic pressing unit may be coupled to the insert through the opening on the outer shell.

The exemplary sperm collector consistent with the disclosed embodiments may include a heating rod. The heating rod may be attached to a center of an inner side of the top end cover. When the top end cover and the container are engaged, the heating rod may be inserted inside the penis insertion passage. When the top end cover is disengaged, the heating rod may be removed from the penis insertion passage.

The heating rod may include a rod body. The rod body may have a chamber therein. In certain embodiments, the rod body has an outer diameter ranging from 16 to 38 mm and a length ranging from 80 to 250 mm. The rod body may also have other dimensions. The rod body may include an electrical heating member and a temperature controller for controlling the electrical heating member. The electrical heating member and the temperature controller may be electrically connected with a power supply. In certain embodiments, the power supply has an output voltage ranging from 2 to 24V. The power supply may have other output voltage. The sperm collector may have a switch to control the heating rod. The electrical heating member may include a tubular member, and a heating chip. The temperature controller may include a temperature sensor and a circuit board.

The exemplary sperm collector consistent with the disclosed embodiments may include a bottom end cover disposed at an end of the container. The power supply may be located on the bottom end cover. The sperm collector may include a charging member. The charging member may be a charging plugholes or charging contacts to electrically connect the power supply to an external power source. The sperm collector may further include a stopper for covering the charging member. In certain embodiments, the charging member is disposed at the bottom end cover.

The container may be formed by connecting a first body formed by a first outer shell and a second body formed by a second outer shell. The first body and the second body may have circular cross sections. The elastic pressing unit may be disposed on the second outer shell. In certain embodiments, the opening on the outer shell may be located on the second outer shell. The opening on the outer shell may be in the shape of rectangle. The opening may also be in other appropriate shapes. The opening in a shape of rectangle may have a length ranging from 30 to 150 mm and a width ranging from 20 to 65 mm. The opening may also have other dimensions. In certain embodiments, two openings are symmetrically arranged on two sides of the second outer shell The exemplary sperm collector consistent with the disclosed embodiments may also include a vibrator. In certain embodiment, the vibrator is disposed at a side of the insert. The vibrator may be an electrical vibrator and electrically connected with the power supply.

The exemplary sperm collector consistent with the disclosed embodiments may include a first attaching member located on the outer shell, and a second attaching member located on the insert. The first attaching member may be engaged with the second attaching member to attach the insert to the outer shell. In certain embodiments, the first attaching member is a locking ring with groove disposed at the outer shell and the second attaching member is an annular groove disposed at the insert at a position corresponding to the locking ring. Other types of attach mechanism may also be used.

The exemplary sperm collector consistent with the disclosed embodiments may include a lubricant pocket located on the insert. In certain embodiment, the lubricant pocket may be located at a position corresponding to the opening on the outer shell. The lubricant pocket may include a releasing opening facing towards the p insertion passage. The releasing opening may be opened when the lubricant pocket receives pressing force to release the content in the lubricant pocket.

An exemplary sperm collector consistent with the disclosed embodiments may provide certain advantages. The user could apply pressure on the penis insertion passage of the sperm collector by pressing the pressing unit. Accordingly, stimulation to penis is increased and better effect of sperm collection may be achieved.

Also, the exemplary sperm collector consistent with the disclosed embodiments may include a heating rod to heat the sperm collector upon engagement of the top end cover. Therefore, a user may feel comfortable when using the sperm collection under relatively low temperature. Better effect of sperm collection could therefore be achieved.

Furthermore, an exemplary sperm collector consistent with the disclosed embodiments may include a power supply with relatively low voltage, such as between 2 to 24 V. Thus, the power supply may have a high heating efficiency, and be safe and reliable. The heating chip and the temperature controller consistent with the disclosed embodiments facilitate the substantially even distribution of heating effect and the substantially precise temperature control. The vibrator may enable a user to reach a climax in relatively short time period. The first attaching member and the second attaching member may attach the insert securely within the inside chamber of the container. The attach mechanism may also provide a convenient way to remove the insert for cleaning. Also, the lubricant pocket may release the content therein when pressed. The content in the lubricant pocket may enhance the sperm collection.

Reference will now be made in detail to exemplary embodiments of the invention, which are illustrated in the accompanying drawings. Wherever possible, the same reference numbers will be used throughout the drawings to refer to the same or like parts.

As shown in FIGS. 1 to 4, an exemplary sperm collector consistent with the disclosed embodiments may include an insert 1 with a penis insertion passage. In certain embodiments, the insert 1 may be made of soft rubber or other appropriate elastic materials. The penis insertion passage is configured to accommodate a male sexual organ.

The sperm collector may also include a container 3. The container 3 may have an outer shell, which forms an inside chamber. The inside chamber is configured to accommodate the insert 1. The sperm collector may include a top end cover 2. The top end cover 2 may engage the container 3 to enclose the inside chamber and the insert 2 may be confined therein. When the top end cover 2 is disengaged, a front end portion of the insert 2 may protrude out of an opening at an upper end of the container 3. The sperm collector may also include a bottom end cover 6.

The sperm collector may include an elastic pressing unit 8. The elastic pressing unit 8 may be made of elastic materials. In certain embodiments, the elastic pressing unit 8 is disposed on the outer shell. The elastic pressing unit 8 may be disposed at a location that is close to the end where the bottom end cover is disposed.

In certain embodiments, the container 3 may be formed by connecting a first body 302 with a first outer shell and a second body 303 with a second outer shell. The first body 302 and the second body 303 may have circular cross sections. The cross section of the first body 302 and the second body 303 may also be in other shapes. In certain embodiments, the first body 302 may have the cross section with a larger diameter at one end and the diameter is gradually reduced towards the end where the first body 302 is attached to the second body 303. The first body 302 and the second body 303 may be connected by an appropriate mechanism such as snap connection, screw connection or glue. Other attachment mechanism may also be used.

Figure 3:
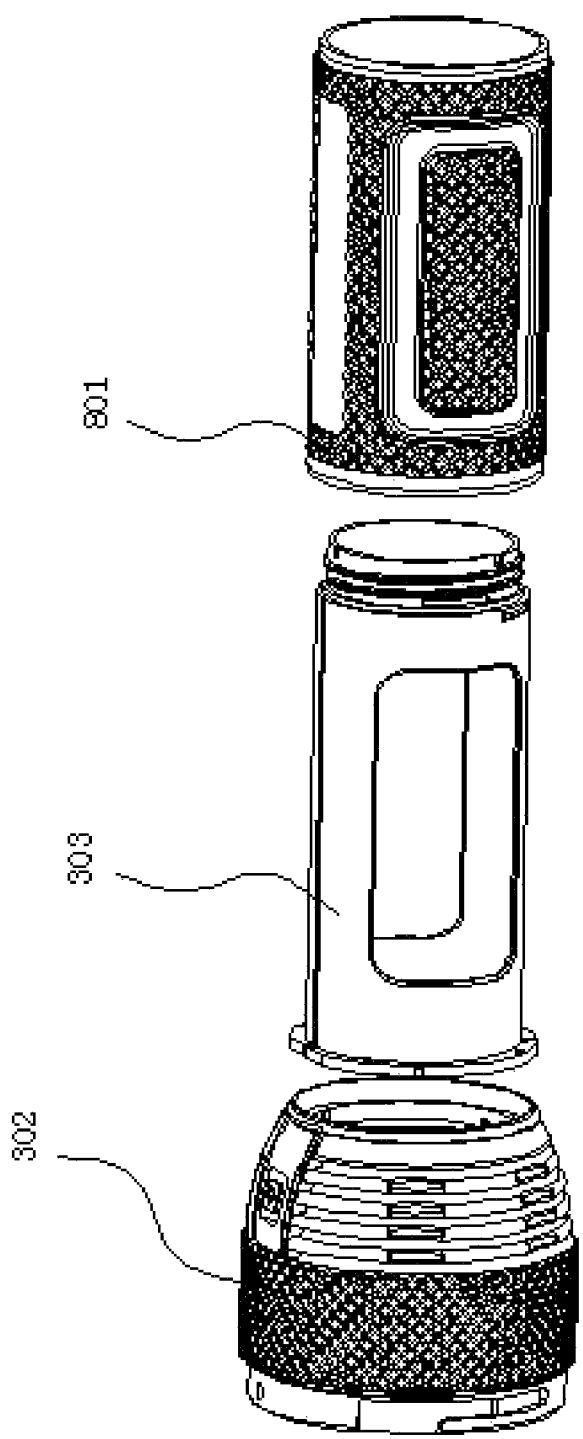
FIG. 3 is a three dimensional illustration of a structure of the container and that of the pressing unit consistent with the disclosed embodiments as shown in FIG. 1 in an exploded view.
Figure 4:
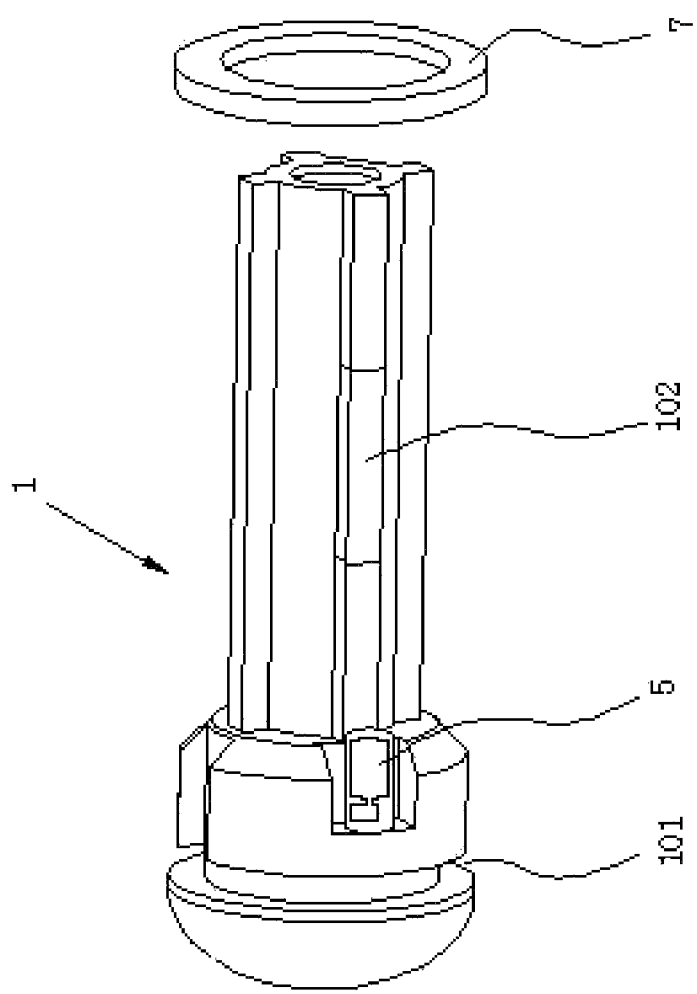
FIG. 4 is a three dimensional illustration of a structure of the insert consistent with the disclosed embodiments as shown in FIG. 1.

As shown in FIG. 3, the container 3 may include an opening on the outer shell. In certain embodiments, the opening is located on the second outer shell of the second body 303. The opening may be in the shape of a rectangle. In certain embodiments, the rectangular opening may have a length ranging from 30 to 150 mm and a width ranging from 20 to 65 mm. The rectangular opening may also have other dimensions. The opening may also be in other appropriate shapes.

The pressing unit 8 may be coupled to the insert 1 through the opening on the outer shell of the container 3. In certain embodiments, the pressing unit 8 may include an elastic sleeve 801. The elastic sleeve 801 may be made of a soft rubber or other appropriate elastic material. The elastic sleeve 801 may surrounds the outer shell of the second body 303. In certain embodiments, there may be two openings on the outer shell of the container 3. The two openings may be symmetrically disposed and configured to transmit the pressure exerted on the elastic sleeve 801. In certain embodiments, the two openings may be located on the second outer shell of the second body 303. When the elastic sleeve 801 is pressed, pressure is transmitted to the insert 1 via the opening on the outer shell and is applied on the penis insertion passage of the sperm collector. Accordingly, stimulation to penis may be increased and good effect of sperm collection may be achieved.

The exemplary sperm collector consistent with the disclosed embodiments may include a vibrator 5. In certain embodiments, the vibrator 5 may be an electrically powered vibrator. Other types of vibrators may also be sued. The vibrator 5 may be disposed on the side of the insert 1. In certain embodiments, two vibrators 5 are disposed symmetrically on two sides of the insert 1. The electrical vibrator 5 may be electrically connected with a power supply. In certain embodiments the power supply is a battery disposed at the bottom end cover 6.

The exemplary sperm collector consistent with the disclosed embodiments may include a vibrator 5. In certain embodiments, the vibrator 5 may be an electrically powered vibrator. Other types of vibrators may also be sued. The vibrator 5 may be disposed on the side of the insert 1. In certain embodiments, two vibrators 5 are disposed symmetrically on two sides of the insert 1. The electrical vibrator 5 may be electrically connected with a power supply. In certain embodiments the power supply is a battery disposed at the bottom end cover 6. In some embodiments, when the vibrator 5 is placed on the side of the insert 1 and the insert 1 is placed in the container 3, the on/off switch 301 may be used to turn the power to the vibrator 5 on or off.

The heating rod may include an electrical heating member and a temperature controller for controlling the electrical heating member. The electrical heating member may include a tubular member 402, and a heating chip 403. In certain embodiments, the heating chip 403 may be made of an elastic material and may surround around an outer surface of the tubular member 402. The temperature controller may include a temperature sensor 404 and a circuit board 405. The electrical heating member and the temperature controller may be electrically connected with a power supply. In certain embodiment, the power supply is a battery disposed at the bottom end cover 6.

The heating rod may include an electrical heating member and a temperature controller for controlling the electrical heating member. The electrical heating member may include a tubular member 402, and a heating chip 403. In certain embodiments, the heating chip 403 may be made of an elastic material and may surround around an outer surface of the tubular member 402. The temperature controller may include a temperature sensor 404 and a circuit board 405. The electrical heating member and the temperature controller may be electrically connected with a power supply. In certain embodiment, the power supply is a battery disposed at the bottom end cover 6. In some embodiments, the top end cover 2 and the heating rod 4 are engaged with container 3, the on/off switch 301 may be used to turn the power to the heating rod 4 on or off.

The exemplary sperm collector consistent with disclosed embodiments may include a first attaching member 7 on an inner wall of the first body 302 and a second attaching member 101 disposed on the insert 1. The insert 1 may be removably attached to the container 3 via the first attaching member 7 and the second attaching member 101. In certain embodiments, the first attaching member 7 is a locking ring and the second attaching member 101 is an annular groove. Other type of attaching mechanism may also be used.

The exemplary sperm collector consistent with disclosed embodiments may include a lubricant pocket 102. The lubricant pocket 102 may be disposed on the insert 1 at a position corresponding to the opening on the outer shell. The lubricant pocket 102 may include a releasing opening facing towards the penis insertion passage. The releasing opening may be closed if no pressure is applied to the insert 1. When the pressing unit 8 is pressed, a pressure may be transmitted and applied on the lubricant pocket and the releasing opening may be opened under pressure and the content therein may be released into the penis insertion passage to lubricate the penis insertion passage to further enhance the effect of sperm collection.

To use the exemplary sperm collection consistent with the disclosed embodiments, the top end cover 2 may be removed. The pressing unit 8 may be pressed to apply pressure on the insert 1. The heating rod 4 may be turned on to increase the temperature in the insert 1. The insert 1 may be inserted into the container 3 and attached to the container 3 by engaging the first attaching member 7 and the second attaching member 101. The releasing opening on the lubricant pocket 102 may be opened under the pressure to release the content therein. The vibrator 5 may be driven to create a vibration. The first attaching member 7 and the second attaching member 101 may be disengaged to remove the insert 1 from the container 3 for cleaning or other purpose.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. For example, the size, shape, and appearance of the sperm collector according to the present disclosure may be modified.

What is claimed is:
1. A sperm collector comprising:
an insert having a penis insertion passage;
a container having an outer shell forming an inside chamber, the outer shell having at least one opening, wherein the inside chamber is configured to accommodate the insert;
a first cover capable of being engaged with the container at a first end of the container;
an elastic pressing unit disposed on the outer shell and coupled to the insert through the opening on the outer shell; and
a heating rod being fixed on the first cover to heat the container,
wherein the elastic pressing unit is configured to transmit pressure to the insert through the opening on the outer shell.

2. The sperm collector according to claim 1, wherein: the heating rod is attached to a center of an inner side of the first cover, and the heating rod is configured to be removably inserted in the penis insertion passage with the first cover being engaged to the container.

3. The sperm collector according to claim 1, the heating rod further comprising: an electrical heating component; and a temperature controller for controlling the electrical heating component.

4. The sperm collector according to claim 3, further comprising: a switch for controlling the heating rod; and a power supply that is electrically connected to the heating component and the temperature controller.

5. The sperm collector according to claim 1, further comprising a second cover capable of being engaged with the container at a second end of the container.

6. The sperm collector according to claim 5, further comprising: a power supply disposed on the second cover.

7. The sperm collector according to claim 6, further comprising: a charging member to electrically connect the power supply to an external power source; and a stopper to conceal the charging member.

8. The sperm collector according to claim 1, further comprising: a first body disposed at the first end of the container; and a second body disposed at a second end of the container, wherein: the opening is located on the second body.

9. The sperm collector according to claim 8, further comprising: a first attaching member located at an inner wall of the first body; and a second attaching member located on the insert, wherein: the first attaching member is capable of engaging the second attaching member to removably attach the insert to the container.

10. The sperm collector according to claim 1, further comprising: a vibrator.

11. The sperm collector according to claim 10, wherein: the vibrator is disposed at a side of the insert.

12. The sperm collector according to claim 1, further comprising: a lubricant pocket located on the insert.

13. The sperm collector according to claim 12, wherein: the lubricant pocket is located to a position corresponding to the opening, and the lubricant pocket includes an opening facing the penis insertion passage, wherein: the opening of the lubricant pocket opens when pressure is applied on the insert to release the content within the lubricant pocket.

* * * * *